(12) United States Patent
Sharp et al.

(10) Patent No.: US 10,576,177 B2
(45) Date of Patent: Mar. 3, 2020

(54) SYSTEMS AND METHODS FOR INSTRUMENT DISINFECTION AND ANTI-MICROBIAL COATING

(71) Applicant: STERIS Instrument Management Services, Inc., Birmingham, AL (US)

(72) Inventors: Gregory Sharp, Birmingham, AL (US); Lloyd Lamar Starks, Spring City, TN (US)

(73) Assignee: STERIS Instruments Management Services, Inc., Birmingham, AL (US)

( * ) Notice: Subject to any disclaimer, the term of this patent is extended or adjusted under 35 U.S.C. 154(b) by 35 days.

(21) Appl. No.: 15/687,657

(22) Filed: Aug. 28, 2017

(65) Prior Publication Data
US 2019/0060497 A1   Feb. 28, 2019

(51) Int. Cl.
*A61L 2/20* (2006.01)
*A61L 2/07* (2006.01)

(52) U.S. Cl.
CPC ....... *A61L 2/20* (2013.01); *A61L 2/07* (2013.01); *A61L 2202/122* (2013.01); *A61L 2202/14* (2013.01); *A61L 2202/24* (2013.01)

(58) Field of Classification Search
CPC . A61L 2/20; A61L 2/202; A61L 2/204; A61L 2/206; A61L 2/208; A61L 2/22; A61L 2202/10; A61L 2202/12; A61L 2202/122; A61L 2202/123; A61L 2202/15; A61L 2202/24; A61L 2/07
See application file for complete search history.

(56) References Cited

U.S. PATENT DOCUMENTS

| | | | | |
|---|---|---|---|---|
| 2002/0044898 | A1* | 4/2002 | Sergio | A61L 2/18 422/300 |
| 2010/0294322 | A1* | 11/2010 | Wagemann | A61L 2/186 134/34 |

* cited by examiner

*Primary Examiner* — Timothy C Cleveland
(74) *Attorney, Agent, or Firm* — C. Brandon Browning; Maynard, Cooper & Gale, PC

(57) ABSTRACT

A disinfection chamber may be configured for receiving a disinfecting vapor from a vapor source and channeling it to contact a surface of an instrument within the chamber. The vapor source may provide the vapor to the disinfecting chamber via an inlet in a chamber cover of the chamber. A vapor core within the disinfecting chamber may channel the vapor from the inlet through a length of the vapor core. A portion of the vapor may pass from an interior of the vapor core and contact the surface of the instrument. When the vapor contacts the surface, the vapor may disinfect the surface, and may deposit an anti-microbial film on the surface.

17 Claims, 6 Drawing Sheets

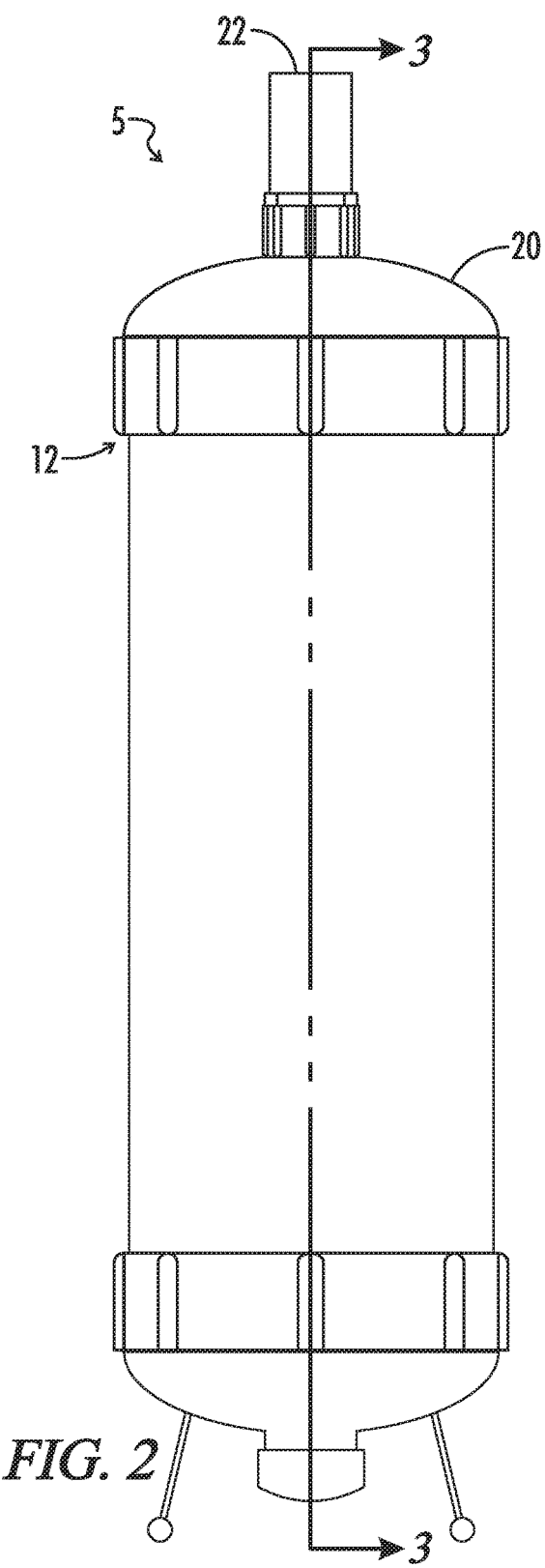
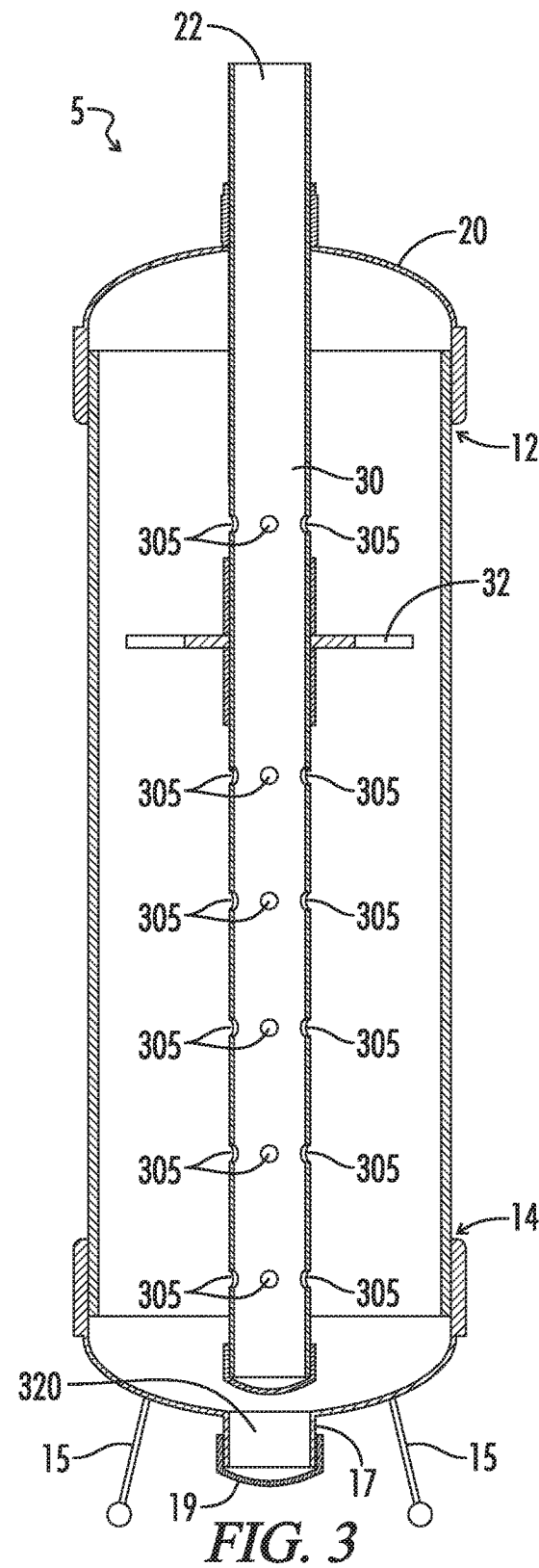
FIG. 2
FIG. 3

SYSTEMS AND METHODS FOR INSTRUMENT DISINFECTION AND ANTI-MICROBIAL COATING

FIELD OF THE INVENTION

The present invention relates to a system for instrument disinfecting and coating, and more particularly, to a chamber body that couples to a removable chamber cover having a vapor inlet for receiving a vapor and a vapor core for channeling the vapor via perforated vapor channel from the vapor inlet to contact a surface of the instrument within the chamber, wherein a surface of the instrument disinfected and an anti-microbial coating is depositing on the surface.

BACKGROUND OF THE INVENTION

Various types of medical devices or instruments, such as metallic syringes, scalpels, forceps, hemostats, and endoscopes may become contaminated as a result of use or exposure to contaminants from time to time. For example, scalpels and forceps may be used for performing medical procedures (e.g., surgical procedures, etc.) during which the scalpel or forceps may come into contact with or otherwise become exposed to contaminants, such as through physical contact with a patient or other potentially contaminated areas. In many applications, only non-contaminated or sterile instruments may be used. Thus, reusable instruments must be disinfected to remove contaminants before they may be suitable for reuse.

Techniques known in the art for disinfecting an instrument's surfaces may include exposing the surfaces to disinfecting conditions, such as high temperatures, sonic waves, or applying a disinfecting substance or solution to a surface of the instrument. Such techniques may include physically applying a disinfecting solution to the surface of the instrument. As an example, instruments may be placed into various apparatuses for exposing the instruments to disinfecting conditions. In some implementations, the disinfection process may require application of a combination of techniques in order to achieve the desired disinfection of the instrument.

Generally, after the instrument has been disinfected, it may remain disinfected until subsequent exposure to contaminants, at which point it must be disinfected again. Steps may be taken to prevent such re-contamination of previously disinfected instruments, such as by separately applying various solutions to the instrument. However, even when such solutions are applied, contamination of a previously disinfected instrument may occur during the time between disinfection and application of the anti-microbial solution. Such contamination may be undetectable to a user, and a risk of use of a contaminated instrument for such applications is increased. Thus, improved techniques preventing contamination of disinfected instruments are generally desirable.

SUMMARY OF THE INVENTION

The present invention is directed to disinfecting chamber, comprising a chamber body; a chamber cover coupled to the chamber body and a vapor source, wherein the chamber cover is coupled to receive a vapor from the vapor source; and a vapor core coupled to the chamber cover, wherein the vapor core channels the vapor to an interior of the chamber body, wherein the vapor core comprises at least one hole for passing the vapor into an interior of the chamber body, wherein the vapor contacts a surface of an instrument within the chamber body, and wherein an anti-microbial film is deposited on the surface of the instrument after the contact. An exemplary vapor comprises a dry steam vapor, and comprises a chitosan solution. An exemplary chitosan solution comprises at most 0.003% chitosan. The chamber may further comprise at least one disc coupled to the vapor core, wherein the disc holds the instrument. According to an aspect of the invention, the instrument may comprise an endoscope, and in some embodiments, the endoscope may be a rigid endoscope.

According to another aspect of the invention, an instrument disinfection system may comprise a vapor source, wherein the vapor source is configured to provide a dry steam vapor, and a disinfecting chamber coupled to receive the vapor from the vapor source, wherein the vapor contacts a surface of an instrument within the chamber, wherein the vapor disinfects the surface of the instrument, and wherein an anti-microbial film is deposited on the surface of the instrument. The system also may comprise a vapor core positioned within the disinfecting chamber, wherein the vapor core comprises a channel for channeling the vapor when received by the vapor core, and wherein the vapor core comprises at least one hole for passing the vapor into an interior of the chamber. The vapor may comprise a chitosan vapor solution, which may be most 0.003% chitosan vapor. The system may further comprise at least one disc coupled to the vapor core, wherein the disc holds the instrument. The instrument may comprise an endoscope, and may be a rigid endoscope.

In yet another aspect of the invention, there is provided, from a vapor source, a vapor for disinfecting a surface of an instrument and depositing an anti-microbial film on the surface. The vapor is received at a disinfecting chamber coupled to receive the vapor from the vapor source. The vapor is passed, from at least one hole of a vapor core within the disinfecting chamber to the interior of the chamber body, wherein the vapor core comprises at least one disc for holding the instrument. The vapor may comprise a dry steam vapor, which may comprise a chitosan vapor solution. The chitosan solution may be at most 0.003% chitosan. In addition, the instrument may be an endoscope.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure.

FIG. 2 depicts a side view of an instrument disinfection system in accordance with some embodiments of the present disclosure.

FIG. 3 depicts a cross-sectional side view of an instrument disinfection system in accordance with some embodiments of the present disclosure.

DETAILED DESCRIPTION

The present disclosure generally pertains to systems and methods for disinfecting and depositing anti-microbial coating on an instrument surface. In some embodiments, a disinfection chamber may be configured for receiving a disinfecting vapor from a vapor source and channeling it to contact a surface of an instrument within the chamber. The vapor source may provide the vapor to the disinfecting chamber via an inlet in a chamber cover of the chamber. A vapor core within the disinfecting chamber may channel the vapor from the inlet through a length of the vapor core. A portion of the vapor may pass from an interior of the vapor core and contact the surface of the instrument. When the vapor contacts the surface, the vapor may disinfect the surface, and may deposit an anti-microbial film on the surface.

Figure 1:
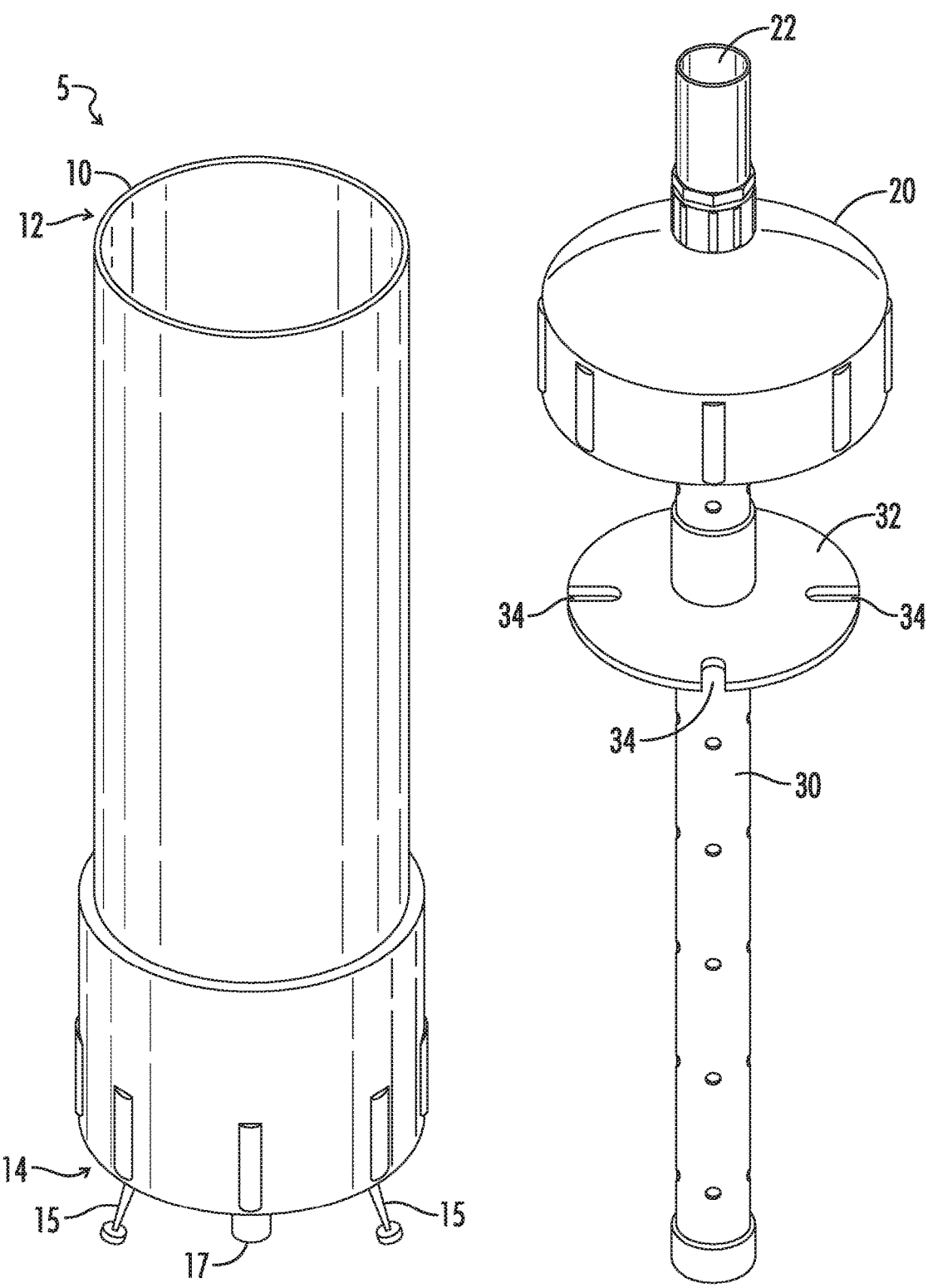
FIG. 1 depicts a three-dimensional perspective view of an instrument disinfection system in accordance with some embodiments of the present disclosure.

FIG. 1 depicts a three-dimensional orthogonal view of an instrument disinfection system 5 in accordance with some embodiments of the present disclosure. The embodiment of system 5 depicted by FIG. 1 has a chamber body 10 and chamber cover 20. The chamber body 10 is configured to couple to chamber cover 20 to form a substantially closed disinfecting chamber, as described further below. An instrument (not specifically shown in FIG. 1) may be held adjacent to a vapor core 30, which may be contained within the chamber body 10 when the chamber cover 20 is coupled to the chamber body 10. A vapor source (not shown in FIG. 1) may provide a disinfecting vapor via an inlet 22 of the chamber cover 20, which may be channeled by the vapor core 30 and passed into an interior of the chamber body 10 to contact a surface of the instrument for disinfecting instrument surface and depositing an anti-microbial film on the surface.

Chamber body 10 may be configured for coupling to the chamber cover 20 and receiving the vapor core 30. As shown in FIG. 1, chamber body 10 may be essentially hollow, and may include a first end 12 configured to couple to the chamber cover 20 and to receive the vapor core 30, and a second end 14 configured to support the chamber body 10. The first end 12 of the chamber body 10 may be substantially open for receiving the vapor core 30 and coupling to the chamber cover 20, and may include various components or be configured suitably for coupling to the chamber cover 20 to achieve the functionality described herein. The second end 14 of the chamber body 10 may have components for supporting the chamber body 10 (e.g., both when coupled to the chamber cover 20 or otherwise), such as one or more legs 15. In some embodiments, the chamber body 10 may include at least one leg 15 adjacent to the second end 14 for supporting the chamber body 10 while simultaneously providing clearance for a chamber drain 17 of the chamber body 10, described in further detail below. In some embodiments, chamber body 10 may have an essentially circular cross-sectional area, and may be configured such that a longitudinal axis of the chamber body 10 is essentially perpendicular to a surface supporting the chamber body 10 (e.g., oriented vertically). The chamber body 10 may have other cross-sectional shapes and may be oriented otherwise in other embodiments, such as for accommodating instruments having other types, sizes, shapes or features.

The chamber body 10 of FIG. 1 is fabricated from a metal, such as an aluminum alloy, but in other embodiments, the chamber body 10 may be fabricated from other materials or combinations of materials and may comprise various components and materials for achieving the functionality described herein. In some embodiments, the chamber body 10 may be fabricated using a combination of various materials suitable for exposure to conditions required of a chamber for disinfecting instruments (e.g., exposure to various temperature, pressure, chemical, or other conditions).

Chamber cover 20 is configured for coupling to the chamber body 10 and configured to receive the disinfecting vapor from a vapor source. The chamber cover 20 has an inlet 22 on a top side of the chamber cover that is configured to receive the vapor, such as by coupling to the vapor source or otherwise. The chamber cover 20 is coupled to a vapor core 30 that is configured to receive vapors from inlet 22 of the chamber cover 20. The vapor core 30 may have a length that corresponds to a length of the chamber body 10, and may be configured to channel the vapor along a length of the vapor core 30 (e.g., along a longitudinal axis of the vapor core 30).

The embodiment of FIG. 1 depicts a disc 32 coupled to the vapor core 30 for holding at least one instrument (not specifically shown in FIG. 1) adjacent to the vapor core 30. As will be described in further detail below, various numbers of shelves 32 may be coupled to the vapor core 30, and may be configured for holding various types and quantities of instruments adjacent to the vapor core 30. Although the disc 32 of FIG. 1 is shown empty, in some embodiments, a portion of the at least one instrument may be loaded (e.g., inserted) into one or more portions of the disc 32 (e.g., slots, holes, or otherwise) such that the at least one instrument is held substantially adjacent to the vapor core 30. FIG. 1 depicts a disc 32 with a plurality of slots 34, but the disc 32 may be configured as having various features for holding various types of instruments, and such features may correspond to a portion and type of instrument to be held. For example, slots 34 may have characteristics (e.g., diameter, width, length, etc.) for accommodating a portion of an endoscope. In some embodiments, the disc 32 may comprise a mesh having holes through which a portion of an instrument may be inserted. Other configurations are possible in other embodiments. In some embodiments, a plurality of vapor cores 30 may be coupled to the chamber cover 20, and each may be coupled to various numbers and types of discs 32 for holding various numbers and types of instruments.

After a desired quantity of instruments has been inserted into portions of the disc 32, the chamber cover 20 may be coupled to the chamber body 10 as depicted in FIGS. 2 and 3. FIG. 2 depicts a side view of the instrument disinfection system 5, and FIG. 3 depicts a cross-sectional side view of the system 5. In some embodiments, chamber cover 20 may be coupled to chamber body 10 by positioning chamber cover 20 over the first end 12 of chamber body 10 and inserting the vapor core 30 within the interior of chamber body 10 until the chamber cover 20 suitably contacts chamber body 10 or is otherwise suitably positioned with respect to the chamber body 10. In some embodiments, the chamber cover 20 may be coupled (e.g., fastened, screwed, latched, etc.) to the chamber body 10 after it has been suitably positioned. Note that cross sectional shapes of the chamber body 10 and chamber cover 20 may generally correspond such that when fitted together, a substantially sealed chamber of system 5 is formed. In this regard, the chamber cover 20 and chamber body 10 may form such a substantially sealed chamber when coupled together, which may be suitable for containing a disinfecting vapor and achieving a desired exposure to the vapor for instruments within system 5.

After the chamber cover 20 has been coupled to the chamber body 10, vapor from a vapor source may be provided to an interior of the chamber body 10 via the inlet 22 of the chamber cover 20. As depicted in FIG. 3, the inlet 22 is configured for receiving the vapor and channeling it to the vapor core 30. In some embodiments, a diameter of the inlet 22 corresponds to a diameter of the vapor core 30, but the inlet 22 may have various suitable cross-sections and configurations in other embodiments. In an exemplary embodiment, the inlet 22 is essentially configured as a tube or conduit to which a vapor source may be coupled (e.g., via hose, tube or otherwise) for receiving and channeling the vapor essentially without leakage or pressure loss between the vapor source and inlet 22. In other embodiments, the inlet 22 may have various components or hardware for coupling to a vapor source, such as a gasket, clamp, collar, or otherwise.

Vapor received via the inlet 22 may be channeled through an interior of the vapor core 30 along a longitudinal axis of the vapor core 30. The vapor core 30 may have a plurality of holes 305 configured to permit vapor to pass from an interior of the vapor core 30 through each of the holes 305. Although a particular number and arrangement of holes 305 is depicted in FIG. 3, various numbers, sizes, configurations and arrangements of the holes 305 are possible in other embodiments. As an example of operation of the vapor core 30, when the vapor is channeled along the vapor core 30 (e.g., as propelled by a force applied to the vapor, via gravity, or otherwise), a portion of the vapor may pass from an interior of the vapor core 30 through one or more holes 305 (e.g., to an interior of the chamber body 10) and may contact a surface of the at least one instrument. In some embodiments, vapor may be provided via the inlet 22 and channeled through the vapor core 30 into the interior of the chamber body 20 for a desired amount of time or until a desired volume of vapor has been introduced into the interior of the chamber (e.g., coupled chamber cover 20 and chamber body 10), such as until substantially all of the interior of the chamber body 10 is filled with vapor or otherwise.

Note that vapor core 30 may have various dimensions relative to the chamber body 10. For example, the vapor core 30 may have a diameter that is sufficiently smaller than a diameter of the chamber body 10 such that a desired quantity of desired instruments may be held (e.g., by disc 32 or otherwise) between an outer surface of the vapor core 30 and an inner surface of the interior of the chamber body 10. In addition, a length (height, when oriented vertically) of vapor core 30 may vary relative to a length (e.g., height when oriented vertically) of chamber body 10. In this regard, vapor core 30 may be configured to fit completely within a chamber formed when the chamber cover 20 and chamber body 10 are coupled together. In addition, as shown by FIG. 3, the vapor core 30 may have a length that permits condensed fluid to escape via a condensate drain 17, as described hereafter. Other dimensions of the vapor core 30 are possible in other embodiments.

The second end of the chamber body 10 shown in the embodiment of system 5 depicted in FIGS. 2 and 3 also has a plurality of legs 15 configured to support the chamber body 10 and a condensate drain 17. Although a particular number of legs 15 is depicted by FIGS. 2 and 3, various numbers of legs 15 may be used in other embodiments as desired to support components of the system 5 as desired and suitably for achieving the functionality described herein. In addition, the condensate drain 17 of FIGS. 2 and 3 is positioned on the second end 14 of the chamber body 10. In some embodiments, the system 5 may be configured to direct condensed fluid from an interior of the chamber cover 20 and chamber body 10 out of the chamber via the drain 17. For example, when disinfecting vapor is introduced into system 5 (e.g., interior of chamber body 10), a condensate may form on an interior surface of the chamber body 10. When the system 5 is oriented such that the second end of the chamber body 10 is below the condensate (e.g., the chamber body is upright), condensate may run along a length of the chamber body 10 and toward and eventually into the drain 17. A cap 19 may be coupled to the drain 17 as desired, and may be configured to prevent escape of substances inside the chamber body 10, to maintain insulation or temperature properties of the system 5, or otherwise. The cap 19 also can be removed as desired for removing substances from the chamber body 10, such as by allowing gravity to remove liquid condensed within the chamber body 10 via the drain 17 or otherwise. In some embodiments, various numbers of drains 17 and respective caps 19 are possible, and may be configured according to various techniques for creating an opening to the interior of the chamber body 10 as may be desired.

Figure 4:
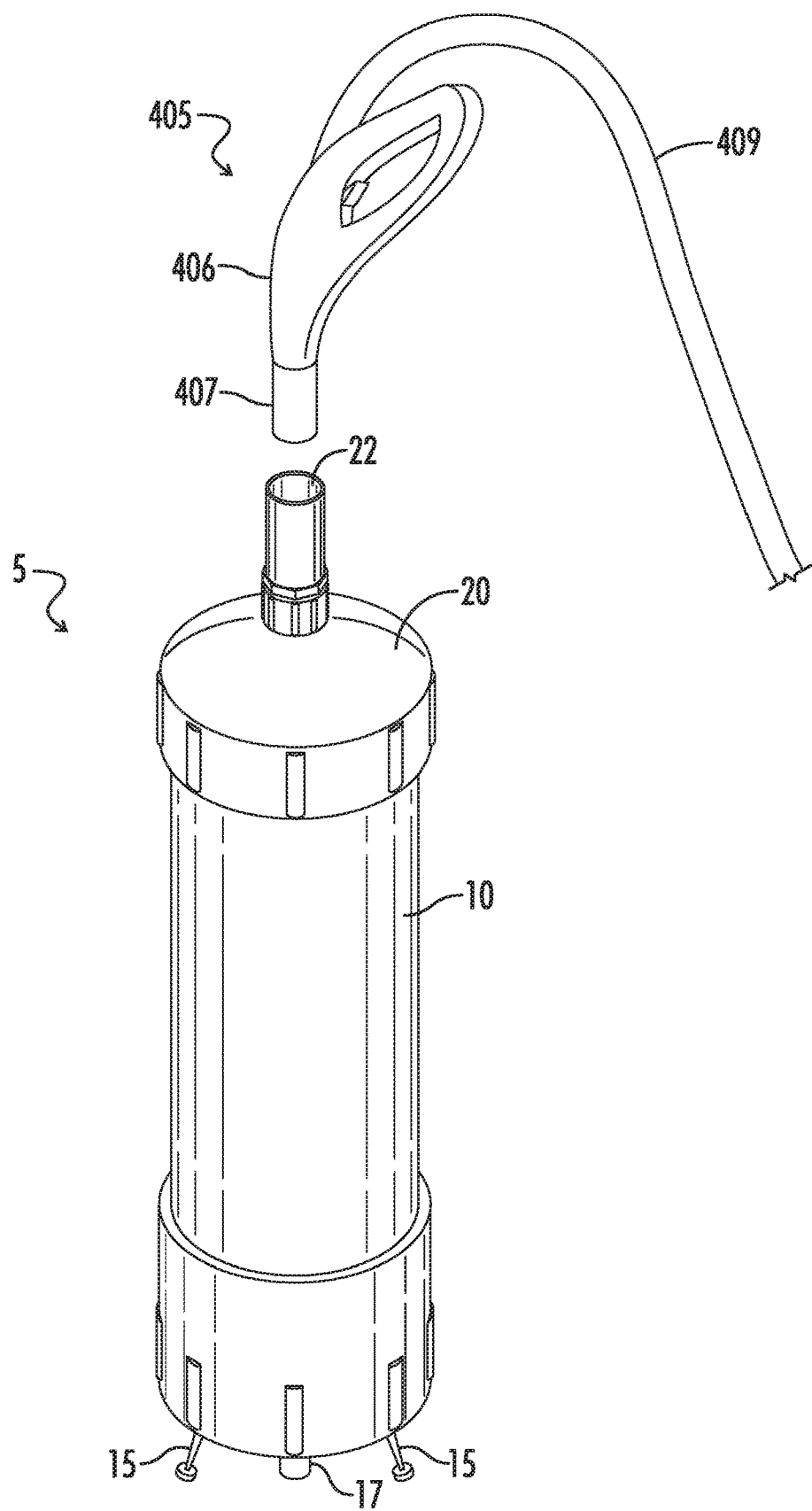
FIG. 4 depicts a three-dimensional perspective view of an instrument disinfection system and vapor source in accordance with some embodiments of the present disclosure.
Figure 5:
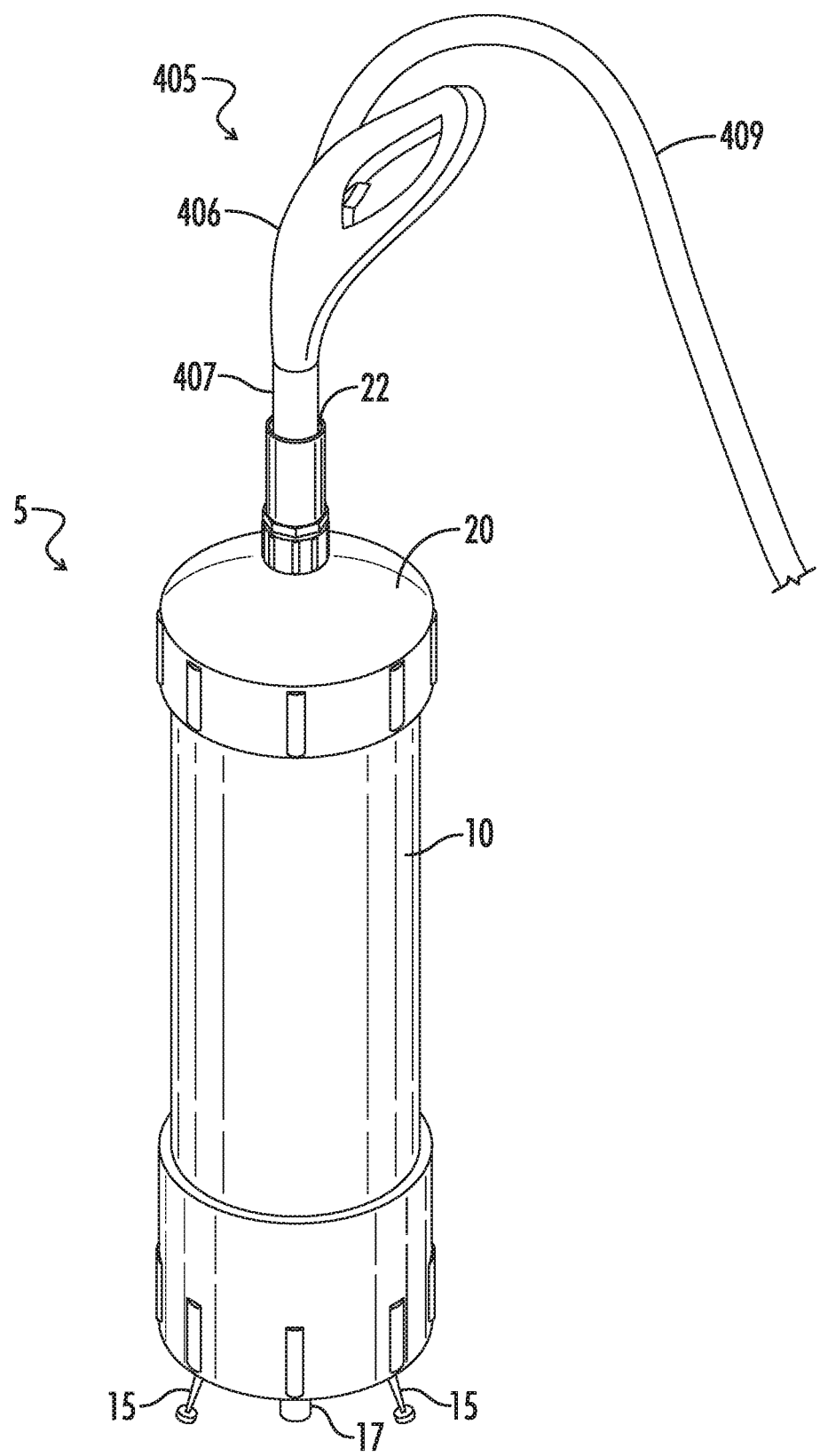
FIG. 5 depicts a three-dimensional perspective view of an instrument disinfection system and vapor source in accordance with some embodiments of the present disclosure.

FIGS. 4 and 5 depict an exemplary disinfection system 5 and vapor source 405 in accordance with some embodiments of the present disclosure. FIG. 4, the vapor source 405 is depicted as detached from the inlet 22 of system 5, as the source 405 may be positioned just before or after coupling to the inlet 22 for providing disinfecting vapor to the system 5. FIG. 5 depicts the vapor source 405 coupled to the inlet 22, such as when providing the vapor. Although particular components of the vapor source 405 are depicted in FIGS. 4 and 5, it will be understood that various components and configurations of each of the system 5 and vapor source 405 may be possible to achieve the functionality described herein.

As noted herein, the vapor source 405 provides a disinfecting vapor, which, in some embodiments, may be configured to chemically disinfect instrument surfaces exposed to the vapor. For example, a desired amount of the disinfecting vapor may be provided from the vapor source 405 to the system 5 (e.g., to the interior of the chamber body 10 via inlet 22 of chamber cover 20 and vapor core 30). The amount may be based on a volume of the system 5, number of instruments for disinfection, or other information. The vapor may be provided to the system 5 so that the instrument surfaces are exposed to the vapor. As described below, the vapor may be provided at a desired temperature and pressure, and the instruments may be exposed to the vapor for a desired amount of time to achieve the desired disinfecting. For example, in some embodiments, where the disinfecting vapor comprises a particular chemical for enhancing disinfection or sterilization of the instruments (e.g., peracetic acid or otherwise), the vapor provided to the system 5 from the vapor source 405 may be provided as a dry steam vapor. The vapor may be introduced to system 5 at a suitable temperature, such as approximately 300° C. or otherwise. The vapor may cool to a temperature of approximately at least 75° C. while inside the system 5 (e.g., chamber body 10), but other temperatures are possible in other embodiments. In addition, in some embodiments, the vapor may be provided from vapor source 405 at a suitable temperature and pressure according to various information, such as regulatory guidelines specifying standards for the respective vapor composition, experimentally determined value ranges or conditions, application-specific conditions, user-defined conditions, or otherwise.

Note that the dry steam vapor may comprise various components (e.g., substances, compounds, chemicals, or other constituent parts) suitable for achieving a desired disinfection or sterilization of an instrument surface. In some embodiments, the vapor may comprise an acid, such as a peracetic acid, for achieving disinfection. A portion of the vapor may be water, such as may be required when the vapor is a dry steam vapor. The vapor may have other components in other embodiments.

In some embodiments, the vapor may comprise a long-chain polysaccharide compound, such as chitosan. The vapor may comprise various amounts of chitosan, but in some embodiments, the chitosan solution may comprise approximately 0.003% chitosan. The vapor may comprise other amounts of chitosan in other embodiments. The vapor comprising chitosan may be provided to the chamber body 10 via the vapor source 405 as described above. In this regard, the vapor may contact the surface of the at least one instrument and thereby disinfect the surface. In addition, the vapor may deposit an anti-microbial film onto the surface of the at least one instrument. In other embodiments, deposition of an anti-microbial film onto an instrument's surface may be performed using other compounds having similar features (e.g., various long-chain polysaccharide compounds).

In some embodiments, the vapor source 405 may be coupled to system 5 to provide the disinfecting vapor addressed above. In the embodiments of FIGS. 4 and 5, vapor source 405 is depicted as a device with a handheld actuator 406 for controlling flow of vapor from within the vapor source 405 into the system 5 via inlet 22, such as by use of a trigger on the actuator 406 or otherwise. In some embodiments, the actuator of vapor source 405 may have a nozzle 407 that may be fitted within inlet 22, which may allow vapor to be pumped or otherwise provided to the chamber cover 20 while reducing or essentially eliminating leakage or pressure loss. In some embodiments, vapor source 405 may be plumbed (e.g., permanently coupled) to the inlet 22 to provide a desired amount of vapor to the system 5 without requiring coupling to the vapor source 405 in each instance. In this regard, additional hardware or components may be required, any of which vapor source 405 may comprise. Vapor source 405 may use other suitable components that correspond to other techniques for providing vapor to the system 5 in other embodiments.

The vapor source 405 has a flexible tube 409 configured to carry the vapor to the system 5 (e.g., inlet 22). In some embodiments, the tube 409 may be coupled to a vapor reservoir of the vapor source 405 (not shown in FIGS. 4 and 5), such as may be used to store an amount of the vapor until use by system 5. In addition, a pump or other power source may be used to propel vapor through the tube 409 and into the system 5. In this regard, the tube 409 may facilitate transportation of the vapor from the vapor reservoir to the system 5, such as by pressurized pumping or otherwise. Vapor source 405 may utilize other components for providing vapor from the vapor reservoir in other embodiments.

Note that the vapor provided from vapor source 405 may be of various types and compositions for disinfecting a surface of an instrument and within the chamber body 10. In an exemplary embodiment, the vapor source 405 is configured for providing a heated, dry steam disinfecting vapor. The vapor may be provided at temperature that exceeds a temperature required for performing disinfection of surfaces of instruments within the system 5, such as at least approximately 75° C. or otherwise. In addition, the vapor may be provided at a desired pressure, such as approximately 1 atmosphere (1 ATM) or otherwise. In this regard, the vapor source 405 may comprise components for ensuring that the vapor is provided at a desired temperature and pressure. In addition, in some embodiments not specifically shown in FIGS. 4 and 5, system 5 may include various components (e.g., pressure sensors, thermocouples, thermometers, etc.) for sensing temperature of the vapor at various locations within system 5, such as within the vapor core 30, chamber body 10, or otherwise. Such components may be coupled to various displays (e.g., gauges, monitors, etc.) for providing output indicative of a sensed temperature, pressure, or other characteristic of the vapor in the vicinity of the respective components. In this regard, a user of system 5 may be able to monitor conditions within the system 5 to ensure that desired conditions and a desired performance of the system 5 are achieved.

Figure 6:
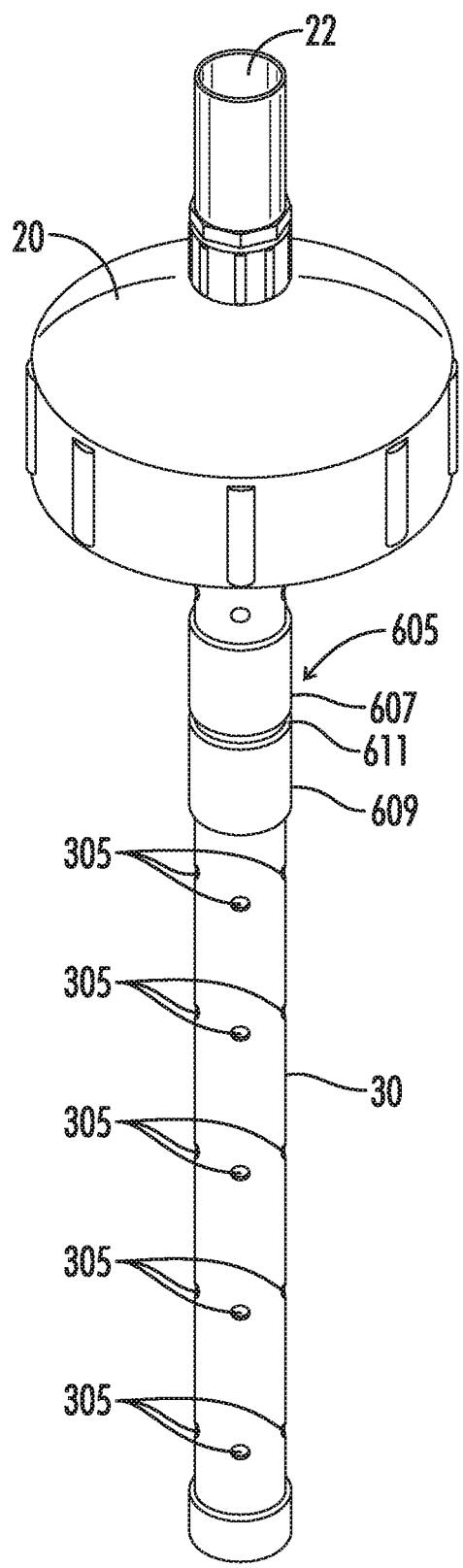
FIG. 6 depicts a three-dimensional perspective view of a chamber cover of an instrument disinfection system in accordance with some embodiments of the present disclosure.
Figure 7:
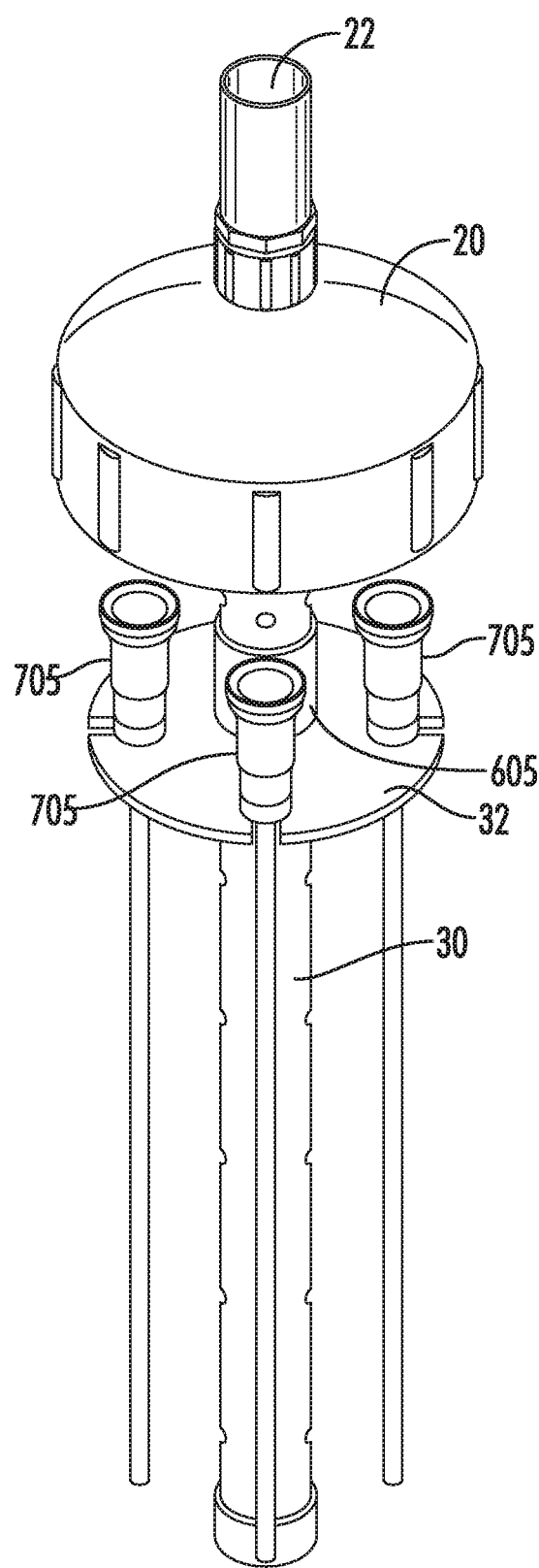
FIG. 7 depicts a three-dimensional perspective view of a chamber cover of an instrument disinfection system holding a plurality of instruments in accordance with some embodiments of the present disclosure.

FIGS. 6 and 7 depict an exemplary vapor core 30 of a disinfection system 5 in accordance with some embodiments of the present disclosure. The vapor core 30 of FIG. 6 is depicted as having a collar 605 configured for coupling to the vapor core 30 and supporting a disc 32 (not specifically shown in FIG. 6). The collar 605 is configured to surround a portion of vapor core 30 and to couple to the vapor core 30 at a desired location along a length of the vapor core 30. In some embodiments, the collar 605 may be movable with respect to the vapor core 30, and may be configured for coupling and decoupling to the vapor core 30 as desired. In some embodiments, system 5 may include a plurality of collars 605 configured for coupling to the vapor core 30, such as for coupling to a corresponding number of discs 32 to achieve holding of a desired number of instruments. It will be appreciated by one skilled in the art upon reading of this disclosure that discs 32 may be coupled to the vapor core or otherwise within the chamber according to other techniques in other embodiments.

The collar 605 of FIG. 6 may comprise an upper portion 607 and lower portion 609, which may be separated by a groove 611. The upper portion 607 and lower portion 609 may have suitable dimensions for supporting a disc 32 that may be configured for holding a desired number of instruments. The groove 611 may essentially comprise a channel having suitable dimensions (e.g., thickness, depth, etc.) for coupling to at least one shelf 32. In some embodiments, the collar 605 may include various components for coupling to the vapor core 30 and for coupling to and supporting disc 32, such as snaps, clips, pins, or otherwise. In this regard, a disc 32 may be coupled to the vapor core 30 via collar 605, and may be movable along the length of the vapor core when the collar 605 is decoupled from the vapor core. Further, in embodiments in which the system 5 comprises a plurality of discs 32, each respective disc 32 may be positioned by positioning its respective collar 605, as desired. Other techniques for coupling a disc 32 to a collar 605 may be possible in other embodiments.

In addition, the vapor core 30 has a plurality of holes 305 that are configured for permitting the disinfecting vapor to pass from an interior of the vapor core 30 to the interior of the chamber body 10 and contacting instruments therein. Vapor may pass through one or more holes 305 at a rate that corresponds to a pressure applied to the vapor (e.g., by vapor source 405 or otherwise). In this regard, the vapor core 30 may channel the vapor along a length of the vapor core 30, and a portion of the vapor may flow through a hole of the vapor core 30. Other portions of the vapor may pass through one or more additional holes 305 until a desired volume of vapor has passed from the vapor core 30 into the interior of the chamber body. Note that the holes 305 may have suitable dimensions and quantities to achieve a desired exposure to the vapor of an instrument within the chamber body 10 (e.g., and chamber cover 20). The vapor core 30 may have various quantities, positions and configurations of holes 305 in some embodiments, and in some embodiments, holes 305 may have varying characteristics (e.g., diameters, positions, etc.) for achieving a desired exposure (e.g., vapor flow through the holes 305).

FIG. 7 depicts an exemplary chamber cover 20 and vapor core 30 having a disc 32 positioned to hold a plurality of instruments 705. The instruments 705 of embodiment of FIG. 7 are depicted as endoscopes, but, as described herein, various types of instruments 705 are possible. The disc 32 of FIG. 7 is configured to hold the endoscopes 705 via a plurality of corresponding slots 34, as depicted in FIG. 1 and described herein. Each endoscope 705 may be held substantially adjacent to the vapor core 30, such that vapor passing from the holes 305 may contact a surface of the endoscopes 705 for performing disinfection and depositing an antimicrobial coating as described herein. In other embodiments, one or more instrument types may be held by one or more discs 32 for achieving the functionality described herein.

In an exemplary operation of the system 5, and as will be described in further detail below, a chamber for disinfecting instruments using a disinfecting vapor may be configured by coupling a chamber cover 20 to a chamber body 10. Before coupling the chamber cover 20 to the chamber body 10, one or more instruments 705 may be loaded into a disc 32 coupled to a vapor core 30 and configured for holding the instruments 705. After the instruments 705 are loaded into the disc 32, the chamber cover 20 may be coupled to the chamber body 10 so that the vapor core 30 and instruments is essentially contained within an interior space of the chamber body 10. In this regard, the instrument 705 held by the disc 32 coupled to the vapor core 30 may be contained within the chamber formed when the chamber cover 20 is coupled to the chamber body 10.

A vapor source 405 may be coupled to the inlet 22 of chamber cover 20 to provide a disinfecting vapor. The vapor may flow (e.g., in response to a pressure applied to the vapor) from vapor source 405 (e.g., via tube 409 in response to operation of the actuator 406) and pass through the inlet 22 and into vapor core 30. The vapor may be that may be channeled along a length the vapor core 30 and passed through holes 305 into the interior of the chamber body 10. The vapor may be dispersed and essentially fill the space within the interior of the chamber body 10. In this regard, the vapor may contact a surface of an instrument 705 within the chamber body 10 (e.g., adjacent to the vapor core 30) to perform desired disinfection of the surface. The chamber body 10 may essentially contain the vapor (e.g., may be pressurized) so that the surface of the instrument 705 may be exposed to the vapor for a desired period of time.

The vapor may be a dry steam vapor, and may comprise a long-chain polysaccharide, such as chitosan. The instrument 705 may be exposed to the vapor for a desired amount of time such that when the vapor contacts surfaces of the instrument 705, the vapor may disinfect the surface of the instrument 705, and may deposit an anti-microbial film onto the surface. In this regard, disinfection and deposition of an anti-microbial film on a surface of an instrument 705 may be accomplished in a single step.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process parameters (e.g., dimensions, configurations, components, process step order, etc.) may be made to further optimize the provided structures, devices and methods, as shown and described herein. In any event, the structures and devices, as well as the associated methods, described herein have many applications. Therefore, the disclosed subject matter should not be limited to any single embodiment described herein, but rather should be construed in breadth and scope in accordance with the appended claims.

What is claimed is:

1. A disinfecting chamber, comprising:
a chamber body having a continuous sidewall defining a longitudinal axis;
a chamber cover coupled to the chamber body;
a vapor core coupled to the chamber cover, wherein the vapor core defines an elongate channel that extends along the longitudinal axis and includes a plurality of holes along a length of the vapor core that fluidly couple the channel to an interior of the chamber body defined between an exterior surface of the vapor core and an interior surface of the continuous sidewall;
a vapor source fluidly coupled to the vapor core, wherein the vapor source includes a dry steam vapor; and
an instrument holder extending radially outward from the vapor core including a first slot arranged for detachably supporting an instrument between the exterior surface of the vapor core and the interior surface of the continuous sidewall.

2. A disinfecting chamber, comprising:
a chamber body having a continuous sidewall defining a longitudinal axis;
a chamber cover coupled to the chamber body;
a vapor core coupled to the chamber cover, wherein the vapor core defines an elongate channel that extends along the longitudinal axis and includes a plurality of holes along a length of the vapor core that fluidly couple the channel to an interior of the chamber body defined between an exterior surface of the vapor core and an interior surface of the continuous sidewall;
an instrument holder extending radially outward from the vapor core including a first slot arranged for detachably supporting an instrument between the exterior surface of the vapor core and the interior surface of the continuous sidewall; and
a vapor source fluidly coupled to the vapor core, wherein the vapor source includes a disinfectant chitosan vapor solution.

3. The chamber of claim 2, wherein the disinfectant chitosan vapor solution comprises at most 0.003% chitosan.

4. The chamber of claim 1, wherein the instrument holder includes at least one disc coupled to the vapor core.

5. The chamber of claim 1, wherein the first slot of the instrument holder supports a first instrument.

6. The chamber of claim 5, wherein the first instrument is an endoscope.

7. A disinfecting chamber, comprising:
- a chamber body having a continuous sidewall defining a longitudinal axis;
- a chamber cover coupled to the chamber body;
- a vapor core coupled to the chamber cover, wherein the vapor core defines an elongate channel that extends along the longitudinal axis and includes a plurality of holes along a length of the vapor core that fluidly couple the channel to an interior of the chamber body defined between an exterior surface of the vapor core and an interior surface of the continuous sidewall; and
- an instrument holder extending radially outward from the vapor core including a first slot arranged for detachably supporting an instrument between the exterior surface of the vapor core and the interior surface of the continuous sidewall;
- wherein the first slot of the instrument holder supports a first instrument and a second slot of the instrument holder supports a second instrument.

8. The chamber of claim 7, wherein a third slot of the instrument holder supports a third instrument and a fourth slot of the instrument holder supports a fourth instrument.

9. The chamber of claim 1, wherein the instrument holder includes a second slot arranged opposite to the first slot.

10. A disinfecting chamber, comprising:
- a chamber body having a continuous sidewall defining a longitudinal axis;
- a chamber cover coupled to the chamber body;
- a vapor core coupled to the chamber cover, wherein the vapor core defines an elongate channel that extends along the longitudinal axis and includes a plurality of holes along a length of the vapor core that fluidly couple the channel to an interior of the chamber body defined between an exterior surface of the vapor core and an interior surface of the continuous sidewall; and
- an instrument holder extending radially outward from the vapor core including a first slot arranged for detachably supporting an instrument between the exterior surface of the vapor core and the interior surface of the continuous sidewall;
- wherein the instrument holder includes a second slot arranged opposite to the first slot and a third slot arranged opposite to a fourth slot.

11. The chamber of claim 1, wherein the plurality of holes are arranged between the longitudinal axis and the interior surface of the continuous sidewall.

12. A disinfecting chamber, comprising:
- an elongate chamber body defining a longitudinal axis;
- a chamber cover coupled to the chamber body;
- a vapor core coupled to the chamber cover, wherein the vapor core defines an elongate channel that extends along the longitudinal axis and includes a plurality of holes along a length of the vapor core that fluidly couple the channel to an interior of the chamber;
- an instrument holder extending radially outward from the vapor core,
- a vapor source fluidly coupled to the vapor core, wherein the vapor source is selected from the group consisting of a dry steam vapor, a disinfectant chitosan vapor solution and a disinfectant chitosan vapor solution including at most 0.003% chitosan; and
- an instrument supported by the instrument holder,
- wherein the longitudinal axis does not extend through the instrument.

13. The chamber of claim 12, wherein the plurality of holes are adapted and arranged to direct a vapor fluid radially outward from the longitudinal axis and onto the instrument.

14. A disinfecting chamber, comprising:
- an elongate chamber body defining a longitudinal axis;
- a chamber cover coupled to the chamber body;
- a vapor core defining an elongate channel that extends along the longitudinal axis and includes a plurality of holes along the vapor core that fluidly couple the channel to an interior of the chamber;
- an instrument holder coupled to the vapor core; and
- a pair of instruments supported by the instrument holder;
- wherein the longitudinal axis does not extend through the instrument holder.

15. The chamber of claim 14, wherein the pair of instruments are arranged opposite one another within the interior of the chamber.

16. The chamber of claim 14, wherein the vapor core has a length that corresponds to a length of the chamber body.

17. The chamber of claim 16, wherein the plurality of holes are adapted and arranged to direct a vapor fluid radially outward from the longitudinal axis along at least half of the length of the vapor core.

* * * * *